United States Patent [19]
DeCoster et al.

[11] Patent Number: 6,103,933
[45] Date of Patent: Aug. 15, 2000

[54] METHODS FOR CONTROLLING THE OXIDATION RATE OF A HYDROCARBON BY ADJUSTING THE RATIO OF THE HYDROCARBON TO A RATE-MODULATOR

[75] Inventors: David C. DeCoster, Buckley; Ader M. Rostami, Bainbridge Island; Mark W. Dassel, Indianola, all of Wash.; Eustathios Vassiliou, Newark, Del.

[73] Assignee: RPC Inc., Atlanta, Ga.

[21] Appl. No.: 08/861,180

[22] Filed: May 21, 1997

Related U.S. Application Data

[60] Provisional application No. 60/030,699, Nov. 7, 1996.

[51] Int. Cl.⁷ .................................................. C07C 61/09
[52] U.S. Cl. ............................................................ 562/509
[58] Field of Search ............................. 562/509; 502/504

[56] References Cited

U.S. PATENT DOCUMENTS

| | | | |
|---|---|---|---|
| 1,121,532 | 12/1914 | Newberry . | |
| 2,014,044 | 9/1935 | Haswell | 75/17 |
| 2,223,493 | 12/1940 | Loder | 260/537 |
| 2,223,494 | 12/1940 | Loder | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/531 |
| 3,290,369 | 12/1966 | Bonfield et al. | 260/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,928,005 | 12/1975 | Laslo | 55/73 |
| 3,932,513 | 1/1976 | Russell | 260/586 |
| 3,946,076 | 3/1976 | Paasen et al. | 260/586 |
| 3,957,876 | 5/1976 | Rapoport et al. | 260/586 |
| 3,987,100 | 10/1976 | Barnette et al. | 260/586 |
| 3,987,808 | 10/1976 | Carbonell et al. | 137/3 |
| 4,032,569 | 6/1977 | Onopchenko et al. | 260/533 C |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,158,739 | 6/1979 | Schulz et al. | 562/543 |
| 4,263,453 | 4/1981 | Schulz et al. | 562/543 |
| 4,308,037 | 12/1981 | Meissner et al. | 55/10 |
| 4,332,590 | 6/1982 | Smith | 23/230 A |
| 4,361,965 | 12/1982 | Goumondy et al. | 34/57 |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,547,905 | 8/1996 | Kulsrestha et al. | 502/66 |
| 5,558,842 | 9/1996 | Vassiliou et al. | 422/108 |
| 5,756,837 | 5/1998 | Costantini et al. | 562/543 |

FOREIGN PATENT DOCUMENTS

| | | | |
|---|---|---|---|
| 0439007A2 | 7/1991 | European Pat. Off. | C07C 68/38 |
| 729 084 A1 | 8/1996 | European Pat. Off. . | |
| 729 085 A1 | 8/1996 | European Pat. Off. . | |
| 0751105A2 | 1/1997 | European Pat. Off. | C07B 33/00 |
| 4426132A1 | 1/1996 | Germany . | |
| 415172 | 8/1934 | United Kingdom | 8132 33 |
| 738808 | 10/1955 | United Kingdom | 2/3 |
| 1143213 | 2/1969 | United Kingdom | 51/16 |
| WO96/03365 | 2/1996 | WIPO . | |
| WO 96/40610 | 12/1996 | WIPO . | |

OTHER PUBLICATIONS

E. Sorribes et al., "Formación de neuvas fases en el proceso de obtención de ácido adípico: causes y efectos que provocan," Rev. R. Acad. Cienc. Exactas, Fis. Nat. Madrid (1987), 81 (1), 233–5 (+English language translation) Jun., 1987.

*Primary Examiner*—Samuel Barts
*Attorney, Agent, or Firm*—Seed Intellectual Property Law Group PLLC

[57] ABSTRACT

Methods for controlling the oxidation rate of a hydrocarbon to an acid by adjusting addition of a rate-modulator are disclosed. In order to control oxidation rate, the ratio of hydrocarbon to rate modulator is appropriately adjusted. Preferably, this ratio is adjusted continually based on feedback relative to oxidation progress parameters. It may be kept substantially constant at steady state conditions of the oxidation, or it may take a path of predetermined values. The rate-modulator preferably comprises a hydrocarbon oxidation initiator.

91 Claims, 3 Drawing Sheets

METHODS FOR CONTROLLING THE OXIDATION RATE OF A HYDROCARBON BY ADJUSTING THE RATIO OF THE HYDROCARBON TO A RATE-MODULATOR

CROSS REFERENCE TO RELATED APPLICATIONS

This application claims priority from U.S. Provisional Application No. 60/030,699 filed Nov. 7, 1996, which application is incorporated herein by reference in its entirety.

TECHNICAL FIELD

This invention relates to methods of making dibasic acids, such as adipic acid for example, by oxidizing a hydrocarbon, such as cyclohexane for example, with a gas containing an oxidant, preferably oxygen.

BACKGROUND OF THE INVENTION

There is a plethora of references (both patents and literature articles) dealing with the formation of intermediate oxidation products, such as diacids, for example, one of the most important being adipic acid. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process," the "Boric Acid Process," and the "Direct Synthesis Process," which involves direct oxidation of cyclohexane to adipic acid with oxygen in the presence of solvents, catalysts, and initiators or promoters.

Initiators or promoters are presently being used to shorten considerably an induction period at the beginning of the reaction. Accepted explanations, which have been given regarding the role of the initiators or promoters, involve oxidation of the catalyst, which is usually cobaltous ions to cobaltic ions.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar" phase. However, no attention has been paid so far to the importance of the two phases, except for separating the adipic acid from the "Polar Phase" and recycling these phases to the reactor partially or totally with or without further treatment. Further, no attention has been paid to the behavior of catalyst, such as solubility, for example, during reaction conditions.

It is also important to note that most, if not all, studies on the Direct Oxidation have been conducted in a batch mode, literally or for all practical purposes.

There is a plethora of references dealing with oxidation of organic compounds to produce acids, such as, for example, adipic acid.

The following references, among the plethora of others, may be considered as representative of oxidation processes relative to the preparation of diacids.

U.S. Pat. No. 5,463,119 (Kollar) discloses a process for the oxidative preparation of $C_5$–$C_8$ aliphatic dibasic acids by
(1) reacting,
 (a) at least one saturated cycloaliphatic hydrocarbon having from 5 to 8 ring carbon atoms in the liquid phase and
 (b) an excess of oxygen gas or an oxygen-containing gas in the presence of
 (c) a solvent comprising an organic acid containing only primary and/or secondary hydrogen atoms and
 (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g. a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of $C_5$–$C_8$ aliphatic dibasic acids through oxidation of corresponding saturated cycloaliphatic hydrocarbons by
(1) reacting, at a cycloaliphatic hydrocarbon conversion level of between about 7% and about 30%,
 (a) at least one saturated cycloaliphatic hydrocarbon having from 5 to 8 ring carbon atoms in the liquid phase and
 (b) an excess of oxygen gas or an oxygen containing gas mixture in the presence of
 (c) less than 1.5 moles of a solvent per mole of cycloaliphatic hydrocarbon (a), wherein said solvent comprises an organic acid containing only primary and/or secondary hydrogen atoms and
 (d) at least about 0.002 mole per 1000 grams of reaction mixture of a polyvalent heavy metal catalyst; and
(2) isolating the C5–C8 aliphatic dibasic acid.

U.S. Pat. No. 5,221,800 (Park et al.) discloses a process for the manufacture of adipic acid is disclosed. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A 1 (Kysela et al.) discloses a method for dehydration of process acetic acid from the liquid-phase oxidation of cyclohexane with air, in the presence of cobalt salt as a catalyst after separation of the adipic acid by filtration and the cyclohexane phase by phase separation, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than about 0.3 to 0.7 wt %.

PCT Demand International Publication WO 96/03365 (Costantini et al.) discloses a method of recycling a cobalt-containing catalyst in a reaction involving the direct oxidation of cyclohexane into adipic acid using an oxygen containing gas. The method is characterized in that the reaction mixture, obtained in a preceding stage where the cyclohexane was oxidized into adipic acid, of which at least part of the intermediate oxidation products, such as cyclohexanol and cyclohexanone, the carboxylic acid and water has been separated and of which at least part of the adipic acid formed has been recovered by crystallization, undergoes at least one extraction operation using at least one cosolvent or a mixture comprising a cosolvent and a carboxylic acid. The method is also characterized by the separation of a mixture containing at least part of the cobalt catalyst, part of the carboxylic acid and optionally residual quantities of other compounds and a solution containing the co-solvent and at least part of the glutaric and succinic acids formed during the oxidation reaction, and the carboxylic acid.

None of the above references, or any other references known to the inventors disclose, suggest or imply, singly or in combination, oxidation of cyclic hydrocarbons to dibasic acids in the presence of initiators by adjusting the ratio of hydrocarbon to initiator, subject to the intricate and critical controls and requirements of the instant invention as described and claimed.

Our co-pending application, Docket No. T-603, of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Acid by Making Phase-related Adjustments," filed on Mar. 6, 1997, and having a Ser. No. 08/812,847, is also incorporated herein by reference.

Our co-pending application, Docket No. T-701, of Mark W. Dassel, David C. DeCoster, Ader M. Rostami, Sharon M.

Aldrich, and Eustathios Vassiliou, titled "Methods and Devices for Preparing Dibasic Acids," filed on Mar. 27, 1997, and having a Ser. No. 08/824,992 is also incorporated herein by reference.

All of the following patent applications, which were filed simultaneously with the present application are also incorporated herein by reference:

Docket No. U.S. patent application Ser. No. 08/859,985 of Eustathios Vassiliou, Mark W. Dassel, David C. DeCoster, Ader M. Rostami, and Sharon M. Aldrich, titled "Methods and Devices for Controlling the Reaction Rate of a Hydrocarbon to an Intermediate Oxidation Product by Pressure Drop Adjustments";

Docket No. U.S. patent application Ser. No. 08/861,281 of Mark W. Dassel, Eustathios Vassiliou, David C. DeCoster, Ader M. Rostami, and Sharon M. Aldrich, titled "Methods and Devices for Controlling the Reaction Rate of a Hydrocarbon to an Intermediate Oxidation Product by Monitoring Flow of Incoming and Outcoming Gases";

Docket No. U.S. patent application Ser. No. 08/861,176 of Mark W. Dassel, Eustathios Vassiliou, David C. DeCoster, and Ader M. Rostari, titled "Methods of Preparing an Intermediate Oxidation Product from a Hydrocarbon by Utilizing an Activated Initiator";

Docket No. U.S. patent application Ser. No. 08/859,890 of Ader M. Rostami, Mark W. Dassel, Eustathios Vassiliou, David C. DeCoster, titled "Methods and Devices for Controlling the Oxidation of a Hydrocarbon to an Acid by Regulating Temperature/Conversion Relationship in Multi-Stage Arrangements"; and Docket No. U.S. patent application Ser. No. 08/861,210 of Eustathios Vassiliou, Ader M. Rostami, David C. DeCoster, and Mark W. Dassel, titled "Pseudo-Plug-Flow Reactor".

SUMMARY OF THE INVENTION

As aforementioned, this invention relates to methods of making dibasic acids by oxidizing a hydrocarbon with a gas containing an oxidant, preferably oxygen. More particularly, it relates to a method of controlling oxidation rate of a C5–C12 cycloaliphatic hydrocarbon to the corresponding dibasic acid, comprising the steps of (a) feeding continually into a reaction zone an oxidant and a rate-modulator in the presence of a catalyst and a solvent, under conditions causing oxidation of the hydrocarbon to the dibasic acid by the oxidant, the hydrocarbon and the rate-modulator being fed at a first ratio, the solvent comprising an organic acid containing only primary and/or secondary hydrogen atoms; and (b) adjusting said first ratio in a manner that the oxidation rate falls within a range of desired values.

The oxidation rate is the amount of hydrocarbon oxidized to organic products, excluding carbon monoxide and dioxide, per unit time.

The first ratio may be adjusted continually based on feedback relative to oxidation progress parameters, or it may be kept substantially constant at steady state conditions of the oxidation, or it may take a path of predetermined values.

It is preferable that the rate-modulator comprises a hydrocarbon oxidation initiator. It is more preferable that the rate-modulator is selected from a group consisting of an aldehyde corresponding to the organic acid of the solvent, a ketone corresponding to the cycloaliphatic hydrocarbon, a peroxide, and a mixture thereof. It is even more preferable that the rate-modulator is selected from a group consisting of an aldehyde corresponding to the organic acid of the solvent, a ketone corresponding to the cycloaliphatic hydrocarbon, and a mixture thereof. It is further even more preferable that the rate-modulator comprises a ketone corresponding to the cycloaliphatic hydrocarbon.

It is also preferable that the rate-modulator comprises cyclohexanone, the aliphatic hydrocarbon comprises cyclohexane, the solvent comprises acetic acid, the oxidant comprises oxygen, and the catalyst comprises cobalt species.

The oxidation rate may be determined by a step of monitoring oxidant depletion in the reaction zone and/or pressure variations in the reaction zone and/or gas flow differentials between gases entering and gases exiting the reaction zone, or by other ways.

The method of this invention may also comprise a step of premixing the rate-modulator with at least one of solvent, catalyst, and hydrocarbon to form a first mixture, and then feeding said first mixture into the reaction zone. Further, the method may comprise a step of atomizing the first mixture in the reaction zone.

The present invention also pertains to a method of controlling the oxidation rate of cyclohexane to adipic acid, comprising the steps of:

(a) partially oxidizing cyclohexane to a second mixture comprising cyclohexanone, the second mixture having a desired second ratio of cyclohexane to cyclohexanone;

(b) feeding the mixture into a reaction zone in the presence of a catalyst, a solvent and an oxidant, and under conditions causing formation of adipic acid;

(c) adjusting said desired second ratio in a manner that the oxidation rate falls within a desired range.

This method may further comprise a step of feeding additional cyclohexane or cyclohexanone to the reaction zone for modifying said desired second ratio to become a desired third ratio.

The second ratio may be adjusted continually based on feedback relative to oxidation progress parameters, or it may be kept substantially constant at steady state conditions of the oxidation, or it may take a path of predetermined values. Further, the third ratio may be adjusted continually based on feedback relative to oxidation progress parameters, or it may be kept substantially constant at steady state conditions of the oxidation, or it may take a path of predetermined values.

As in the previous case, the oxidation rate may be determined for example by a step of monitoring oxidant depletion in the major reaction zone and/or pressure variations in the major reaction zone and/or gas flow differentials between gases entering and gases exiting the major reaction zone. Also, this method may further comprise a step of atomizing the second mixture in the major reaction zone.

The desired range of the second ratio preferably falls between 99.5/0.5 and 95/10. However, this also depends on whether cyclohexane or cyclohexanone or a combination of cyclohexane and cyclohexanone are also fed directly to the major reaction zone. Under such circumstances the above mentioned preferable limits of 99.5/0.5 and 95/10, are adjusted accordingly to take into account such additional feeding.

It is extremely important to continually control the ratio of hydrocarbon to rate modulator, such as for example an oxidation initiator like cyclohexanone for example, not only in order to control the oxidation rate, but also to ensure that the selectivity and/or yield to the desired oxidation product, such adipic acid for example does not suffer.

It was found unexpectedly by the inventors that in certain ranges of hydrocarbon to rate modulator ratios, the selectivity starts suffering considerably, although the oxidation rate increases. For example, in the case that the hydrocarbon is cyclohexane, the rate modulator is cyclohexanone, and the desired oxidation product is adipic acid, ratios of hydrocarbon to rate modulator lower than 80/20 deteriorate the selectivity considerably. Thus, it is of utmost importance that the modulation of the oxidation rate is limited to ranges at which the selectivity is not deteriorated excessively. A balance of reaction rate and selectivity may be determined in each particular case and the appropriate range of hydrocarbon to rate modulator be employed.

The oxidation may take place in a preceding reaction zone and in the major reaction zone, the preceding reaction zone being at a higher temperature than the major reaction zone.

Further, the instant invention pertains to a method, wherein the dibasic acid comprises a compound selected from a group consisting of adipic acid, phthalic acid, isophthalic acid, and terephthalic acid, and the method further comprises a step of reacting acid with a third reactant selected from a group consisting of a polyol, a polyamine, and a polyamide in a manner to form a polymer of a polyester, or a polyamide, or a (polyimide and/or polyamideimide), respectively.

The method may further comprise a step of spinning the polymer into fibers.

The instant invention, also encompasses a device for controlling the oxidation rate of a C5–C12 cycloaliphatic hydrocarbon to the corresponding dibasic acid, comprising:
  a major reaction chamber;
  first feeding means for feeding into the major reaction chamber the cycloaliphatic hydrocarbon;
  second feeding means for feeding continually into the major reaction chamber an oxidation rate-modulator;
  third feeding means for feeding into the major reaction chamber an oxidant;
  fourth feeding means for feeding into the major reaction chamber a catalyst and a solvent, the solvent comprising an organic acid containing only primary and/or secondary hydrogen atoms;
  condition controlling means for controlling conditions in the major reaction chamber in a manner to induce oxidation of the hydrocarbon by the oxidant;
  ratio adjusting means for causing the hydrocarbon and the rate-modulator to be fed into the major reaction chamber at a first ratio, and
  optionally adjusting said first ratio in a manner that the oxidation rate falls within a range of desired values.

This device may further comprise feedback means connected to the major reaction chamber, and the ratio adjusting means may be adapted to adjust the first ratio continually based on feedback from the feedback means, the feedback being relative to oxidation progress parameters.

The feedback preferably comprises means for monitoring oxygen depletion during the oxidation and/or pressure variations in the major reaction chamber and/or gas flow differentials between gases entering and gases exiting the major reaction chamber.

The ratio adjusting means may be adapted to maintain the first ratio substantially constant at steady state conditions of the oxidation, or to guide the first ratio through a path of predetermined values, among other variations.

Further, the device of the present invention may comprise premixing means for premixing the rate-modulator with at least one of solvent, catalyst, and hydrocarbon to form a first mixture, and then feeding said first mixture into the major reaction chamber. Preferably the device may also comprise atomizing means for atomizing the first mixture in the major reaction chamber.

A different embodiment of the present invention involves a device for controlling the oxidation rate of cyclohexane to adipic acid, comprising in combination an assembly of:
  a precursory reaction chamber;
  first cyclohexane feeding means for feeding cyclohexane into the precursory reaction chamber;
  first oxidant feeding means for feeding an oxygen containing gas into the precursory reaction chamber in order to partially oxidize the cyclohexane to a second mixture comprising cyclohexanone, the second mixture having a desired second ratio of cyclohexane to cyclohexanone;
  a major reaction chamber;
  second mixture feeding means for feeding the second mixture into the major reaction chamber;
  additional feeding means for feeding one or more of a catalyst, a solvent and an oxidant into the major reaction chamber;
  condition controlling means for controlling conditions in the major reaction chamber in a manner to induce oxidation of the hydrocarbon by the oxidant; and
  ratio adjusting means for adjusting said second ratio in a manner that the oxidation rate falls within a range of desired values.

This device may further comprise a second cyclohexane feeding means for feeding cyclohexane to the major reaction chamber for modifying said desired second ratio to become a desired third ratio.

It is further preferable that the device further comprises feedback means connected to the major reaction chamber, and wherein the ratio adjusting means are adapted to adjust the second and/or ratio continually based on feedback from the feedback means, the feedback being relative to oxidation progress parameters in the major reaction chamber. More preferably, the feedback means are adapted to monitor oxygen depletion during the oxidation and/or pressure variations in the major reaction chamber and/or gas flow differentials between gases entering and gases exiting the major reaction chamber.

The ratio adjusting means may be adapted to maintain the second ratio substantially constant at steady state conditions of the oxidation, or to guide the second ratio through a path of predetermined values.

The device may further comprise premixing means for premixing the second mixture with at least one of solvent, catalyst, cyclohexane, and cyclohexanone to form a third mixture, and then feeding said third mixture into the major reaction chamber. The device preferably further comprises atomizing means for atomizing the third mixture in the major reaction chamber.

Further, this invention pertains to a device for controlling the oxidation rate of a C5–C12 cycloaliphatic hydrocarbon to the corresponding dibasic acid, comprising:
  a preceding reaction chamber;
  first feeding means for feeding into the preceding reaction chamber the cycloaliphatic hydrocarbon;
  second feeding means for feeding continually into the preceding reaction chamber a oxidation rate-modulator;
  third feeding means for feeding into the preceding reaction chamber an oxidant;
  fourth feeding means for feeding into the preceding reaction chamber a catalyst and a solvent, the solvent comprising an organic acid containing only primary and/or secondary hydrogen atoms;
  a major reaction chamber connected to the preceding reaction chamber in a manner that contents of the preceding reaction chamber may move to the major reaction chamber;

means for maintaining the temperature of the preceding reaction chamber higher than the temperature of the major reaction chamber; and ratio adjusting means for causing the hydrocarbon and the rate-modulator to be fed to the preceding reaction chamber at a first ratio, and optionally adjusting said first ratio in a manner that the oxidation rate in the major reaction chamber falls within a range of desired values.

The lower conversions per stage, according to this invention, simplify the heat transfer problems as well as the design of each reaction chamber. Furthermore, they provide better energy efficiency.

BRIEF DESCRIPTION OF THE DRAWINGS

The reader's understanding of this invention will be enhanced by reference to the following detailed description taken in combination with the drawing figures, wherein.

DETAILED DESCRIPTION OF THE INVENTION

Figure 1:
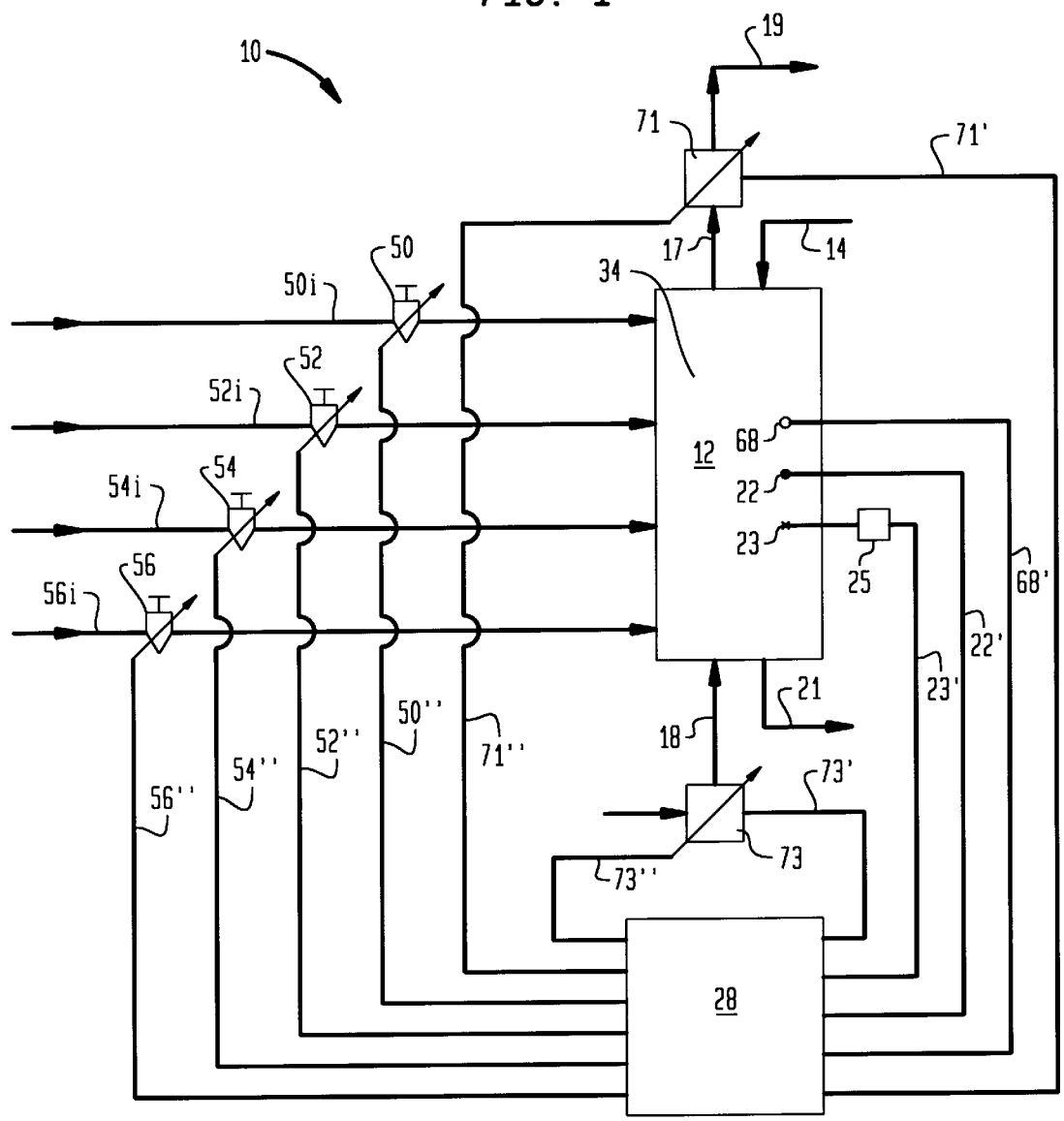
FIG. 1 illustrates schematically a preferred embodiment of the present invention comprising a major reaction chamber 12.

As mentioned earlier, this invention relates to methods of making intermediate oxidation products, such as acids, for example, by oxidizing a hydrocarbon with a gas containing an oxidant, preferably oxygen.

After a reaction has taken place in the Direct Synthesis of cyclohexane to adipic acid, a mixture of two liquid phases is present at ambient temperature, along with a solid phase mainly consisting of adipic acid. The two liquid phases have been called the "Polar Phase" and the "Non-Polar" phase. However, no attention has been paid so far to the importance of the two phases, except for separating the adipic acid from the "Polar Phase" and recycling these phases to the reactor partially or totally with or without further treatment.

For purposes of clarity and brevity, the most preferred constituents may be used to exemplify the methods of the present invention, instead of more generic terms. For example "acetic acid" may be used instead of "solvent," but it should be understood that any other suitable solvent(s) may be used in said methods. Examples of less preferred solvents are butyric acid, propionic acid, etc. In a similar manner, "acetaldehyde" may be used instead of the more generic name "initiator" or "promoter," and "cobalt acetate tetrahydrate," or "cobalt acetate" (both meaning "cobaltous acetate tetrahydrate" unless otherwise specified) may often be used instead of the more generic term "catalyst."

In addition to the formation of adipic acid, the methods of the present invention may also be applied to other diacids from the corresponding cyclic aliphatic hydrocarbons. Examples are formation of glutaric acid from cyclopentane, formation of pimelic acid from cycloheptane, and the like.

As aforementioned, initiators have been used so far to initiate a reaction, such as oxidation of cyclohexane to adipic acid, for example. This initiation of reaction or oxidation shortens an induction period considerably. The induction period in their absence is in most occasions unacceptably long, frequently of the order of days, while in their presence, the induction period is rather short, frequently of the order of a fraction of one hour. The explanation accepted by many researchers is that the initiators induce oxidation of the catalyst, which usually comprises cobaltous ions, to cobaltic ions. Cobaltic ions are necessary in the mechanism of oxidations, such as the oxidation of cyclohexane to adipic acid for example. After a certain amount of cobaltic ions have been formed, the mechanisms proposed involve a combination of cobaltous and cobaltic ions, both of which are considered as being regenerated through formation of intermediate species during the oxidation. Initiators in the production of cyclic alcohols or ketones may be added to the reactants at the start or continuously during the oxidation or both.

It was found unexpectedly by the inventors that initiators may beneficially be used continually to control the rate of oxidation, and that they may be used as oxidation rate modulators. Oxidation rate modulators are defined, according to the instant invention, as compounds, the continual addition of which in a reaction zone or a reaction chamber may change controllably the rate of oxidation, in a manner that the oxidation rate attains a value within a desired or predetermined range of values.

Compounds which may be used as oxidation rate modulators, or simply rate modulators, include but are not limited to oxidation initiators, such as for example, acetaldehyde, cyclohexanone, methylethylketone, etc.

It is extremely important to continually control the ratio of hydrocarbon to rate modulator, such as for example an oxidation initiator like cyclohexanone for example, not only in order to control the oxidation rate, but also to ensure that the selectivity and/or yield to the desired oxidation product, such adipic acid for example does not suffer.

It was found unexpectedly by the inventors that in certain ranges of hydrocarbon to rate modulator ratios, the selectivity starts suffering considerably, although the oxidation rate increases. For example, in the case that the hydrocarbon is cyclohexane, the rate modulator is cyclohexanone, and the desired oxidation product is adipic acid, ratios of hydrocarbon to rate modulator lower than 80/20 deteriorate the selectivity considerably. Thus, it is of utmost importance that the modulation of the oxidation rate is limited to ranges at which the selectivity is not deteriorated excessively. A balance of reaction rate and selectivity may be determined in each particular case and the appropriate range of hydrocarbon to rate modulator be employed.

In such oxidations, a solvent is involved, such as acetic acid for example. If an aldehyde is used as a rate modulator, it is preferable that the aldehyde corresponds to the acid used as solvent in the oxidation reaction. If acetic acid is the solvent used in the oxidation, for example, acetaldehyde should preferably be used as a rate modulator. Similarly, if an aldehyde is to be used in an oxidation as a rate modulator, and if the solvent is propionic acid, the aldehyde corresponding to propionic acid should be preferably utilized. The use of acetic acid as solvent is highly preferred, because it is considerably more stable than other organic acids. Use of the corresponding aldehyde is preferable because if oxidized it turns to the corresponding acid. Thus, if acetaldehyde is used as a rate modulator, and if it is oxidized it turns to acetic acid which is the solvent.

In a similar manner, if a ketone is used as the rate modulator, it is preferable that the ketone corresponds to the hydrocarbon which is to be oxidized. Thus, in the case that the hydrocarbon to be oxidized to adipic acid is cyclohexane, the preferable ketone to be used as a rate modulator should be cyclohexanone. Use of cyclohexanone as a rate modulator, in the case of direct synthesis of adipic acid, is of particular interest because cyclohexane may initially be partially oxidized to form just a small appropriate amount of cyclohexanone, and then further oxidized to adipic acid.

Control of the oxidation rate is of utmost importance. A delicate balance between yield and oxidation rate exists, depending on the particular circumstances. If the oxidation rate is unacceptably high, low yields may be observed, and even explosions may occur. On the other hand, if the oxidation rate is too low, the production rate is also too low, and even with 100% yield the process may be grossly uneconomical. This delicate balance may be easily determined for any particular circumstances, and optimized. What is important is to be able to control the oxidation rate within a desired range, depending on the particular circumstances.

A preferred embodiment of this invention is illustrated in FIG. 1. In FIG. 1, there is depicted a device or continuous reactor system 10 comprising a major reaction chamber 12, which includes a major reaction zone 34.

Connected to the major reaction chamber 12 are a hydrocarbon feeding line 50$i$; a solvent feeding line 52$i$; a catalyst feeding line 54$i$; a rate modulator (which may be an initiator or promoter) feeding line 56$i$; a gaseous oxidant feeding line 18; a gas outlet line 17; a predominantly non-gas outlet line 21; a recycle feeding line 14; a pressure monitor 68; a temperature monitor 22; and an optional oxygen monitor or analyzer 25, which samples preferably the vapor contents of the major reaction chamber 12 through orifice 23.

The gas outlet 17 is also connected to a gas outlet assembly 71 which may comprise a controllable assembly of condenser(s) for removing condensible matter, valve(s), flowmeter(s) and the like (not shown for purposes of clarity), similar to the ones described in our aforementioned co-pending applications and/or issued patents. The gas inlet 18 is also connected to a gas inlet assembly 73, which may comprise a controllable assembly of valve(s), flowmeter(s) and the like for providing a gaseous oxidant to the major reaction chamber, and it may be similar to the ones described in our aforementioned co-pending applications and/or issued patents. Both the inlet assembly 73 and the outlet assembly 71 are controlled and also give flow rate feedback data to a controller 28, which is preferably a computerized controller.

The controller 28 also controls a number of valves 50, 52, 54, and 56 through output lines 50", 52", 54", and 56", respectively, which valves in turn regulate the flow of ingredients through inlet lines 50$i$, 52$i$, 54$i$, and 56$i$, respectively.

The thermocouple or temperature monitor 22, the pressure monitor 68, and the oxygen monitor 25 give information to the controller 28 regarding temperature, pressure and oxygen content respectively. The oxygen analyzer may be any well known to the art oxygen analyzer.

A flowmeter in each of the inlet lines 50$i$, 52$i$, 54$i$, and 56$i$, is not shown in FIG. 1 for purposes of clarity. Their purpose is to give flow information to the controller 28, useful for the regulation of valves 50, 52, 54, and 56 so that they deliver a desired flow for each ingredient.

Lines 50$i$, 52$i$, 54$i$, and 56$i$, may be heated by well known to the art techniques, or as described in our co-pending applications, and/or patents, individually or collectively or otherwise. These lines may also merge, if so desired, and their contents premixed before entering the major reaction chamber 12.

The major reaction chamber 12 may be a stirred tank reactor, a recirculation reactor, an atomization reactor, or other type of reactor known to the art.

Monitors (not shown) for carbon monoxide, carbon dioxide, oxygen, and/or other gases may also be placed preferably in one of the of gas lines 17 or 19.

In operation of this embodiment, hydrocarbon, cyclohexane for example, solvent, acetic acid for example, catalyst, cobalt acetate tetrahydrate for example, preferably in the form of a solution comprising solvent for example, and a rate modulator, such as an oxidation initiator or promoter, like cyclohexanone or acetaldehyde, for example enter the major reaction chamber 12 as disclosed in our our co-pending applications, and/or patents. At the same time that the aforementioned ingredients enter the major reaction chamber 12, a gaseous oxidant also enters through line 18, and starts reacting with the hydrocarbon. No recyclables exist at the initial stages.

After the reaction has been initiated a certain flow of predominantly non-gaseous matter is initiated through line 21, which matter contains products of oxidation, by-products, and unreacted ingredients. The flow is arranged so that a desired conversion of hydrocarbon to acid, depending on the particular circumstances, but usually between 5% and 50%, has been attained. In the case of atomization reactors, the ingredients, including recyclables, are preferably premixed before entering the major reaction chamber 12. The products may be separated products from by-products and recyclables at a further stage, similar to the stages disclosed in our co-pending applications and/or patents. The recyclables may enter the major reaction chamber 12 through inlet line 14. Of course, line 14 may be merged with one or more of lines 50$i$, 52$i$, 54$i$, and 56$i$, before a mixture of the respective ingredients enters the major reaction chamber 12.

The temperature in the major reaction chamber 12 is monitored by one or more thermocouples or temperature monitors 22, and the controller adjusts the heat flow to or from the major reaction chamber in a manner that a temperature within a desired range is maintained. The heat flow may be controlled either through heaters (not shown) on the individual lines 50$i$, 52$i$, 54$i$, 56$i$, and 14, or directly by heating or cooling the major reaction chamber 12 itself, or by other methods well known to the art.

The controller, based on information regarding oxygen consumption, which is representative of oxidation rate, especially after correction for carbon monoxide and carbon dioxide formation, adjusts the ratio of hydrocarbon to rate modulator entering the major reaction chamber 12 so that the reaction or oxidation rate is maintained within desired limits. The adjustment is predominantly made by regulating 50 and 56 after taking into account the composition of the recyclables.

If the rate of oxidation is too high, the controller 28 changes the settings of valves 50 and 56 so that the ratio of hydrocarbon to rate-modulator is increased. Similarly, if the rate of oxidation is too low, the controller 28 changes the settings of valves 50 and 56 so that the ratio of hydrocarbon to rate-modulator is decreased.

If the reaction has reached steady conditions of oxidation, meaning that among other parameters the rate of oxidation attains a substantially constant value, and if this value remains within the desired range, the hydrocarbon to rate modulator ratio may remain also substantially constant.

Further, it may be preferable, under certain circumstances, that the hydrocarbon to rate-modulator ratio takes a path of predetermined values in a manner that the desirable range of values of the rate of oxidation follows also a desired path. For example, especially in the case of a batch or semi-batch reactor, it may be desirable that at the beginning a low ratio is employed, which becomes higher toward the end of the reaction, for achieving better yield for example.

In the case that the hydrocarbon is cyclohexane and the rate-modulator is cyclohexanone, an initial ratio of 97 to 3 is preferable. As the oxidation proceeds, the ratio may preferably be varied in the range of 99.9/0.1 to 80/20, and more preferably in the range of 99/1 to 90/10. Ratios lower than 80/20 usually produce large amounts of undesired by-products, while ratios higher than 99.9/0.1 are ineffective.

Changes and adjustments in the ratio of hydrocarbon to rate-modulator are preferably made in frequency of time increments ranging from 1/5 to 1/50 of the hold-up time of the contents of the major reaction chamber 12 in the case of stirred tank reactors. The controller 28 may control the timing, frequency and magnitude of such changes and adjustments, depending on the dynamics of the system, according to a desired program. If the feedback to the controller shows large effects with an adjustment, the frequency of a next adjustment is preferably decreased and/or the magnitude of the adjustment is also decreased. Similarly, if the feedback to the controller shows small effects with an adjustment, the frequency of a next adjustment is preferably increased and/or the magnitude of the adjustment is also increased. Hold up time is the time that it would take for a reaction chamber to be emptied at the flow rate of line 21, with nothing being added to the reaction chamber.

The oxidation rate may be calculated by the controller by measuring the oxidant, preferably oxygen, entering through line 18, the oxidant leaving through line 17, and formation of carbon monoxide and carbon dioxide. The oxidant coming into the major reaction chamber through line 18 and leaving through line 17 may be measured as described in our co-pending application referenced above, Ser. No. 08/861,281. The oxidation rate may also be determined by measuring the pressure drop rate at different time intervals as described in our co-pending application referenced above, Ser. No. 08/859,985. The oxidation rate may also be calculated by measuring the consumption of oxidant, by means of monitor 25, after the entering and exiting of oxidant is stopped for short periods of time. One measurement of oxidant may be taken at the beginning of such period, and one at the end of the period. The difference, shows the consumption of oxidant at this period of time. The oxidant monitor may be positioned on line 17 or 19, and the content of oxidant monitored. From the difference of this content and the amount of oxidant entering the major reaction chamber, the controller calculates the rate of oxidant consumption and the oxidation rate from the oxidant consumption rate. In all cases, the amounts of carbon dioxide and carbon monoxide formed are preferably monitored and taken into account for the oxidation rate calculation by the controller, unless these amounts of carbon dioxide and carbon monoxide are either too small or constant for all practical purposes.

Figure 2:
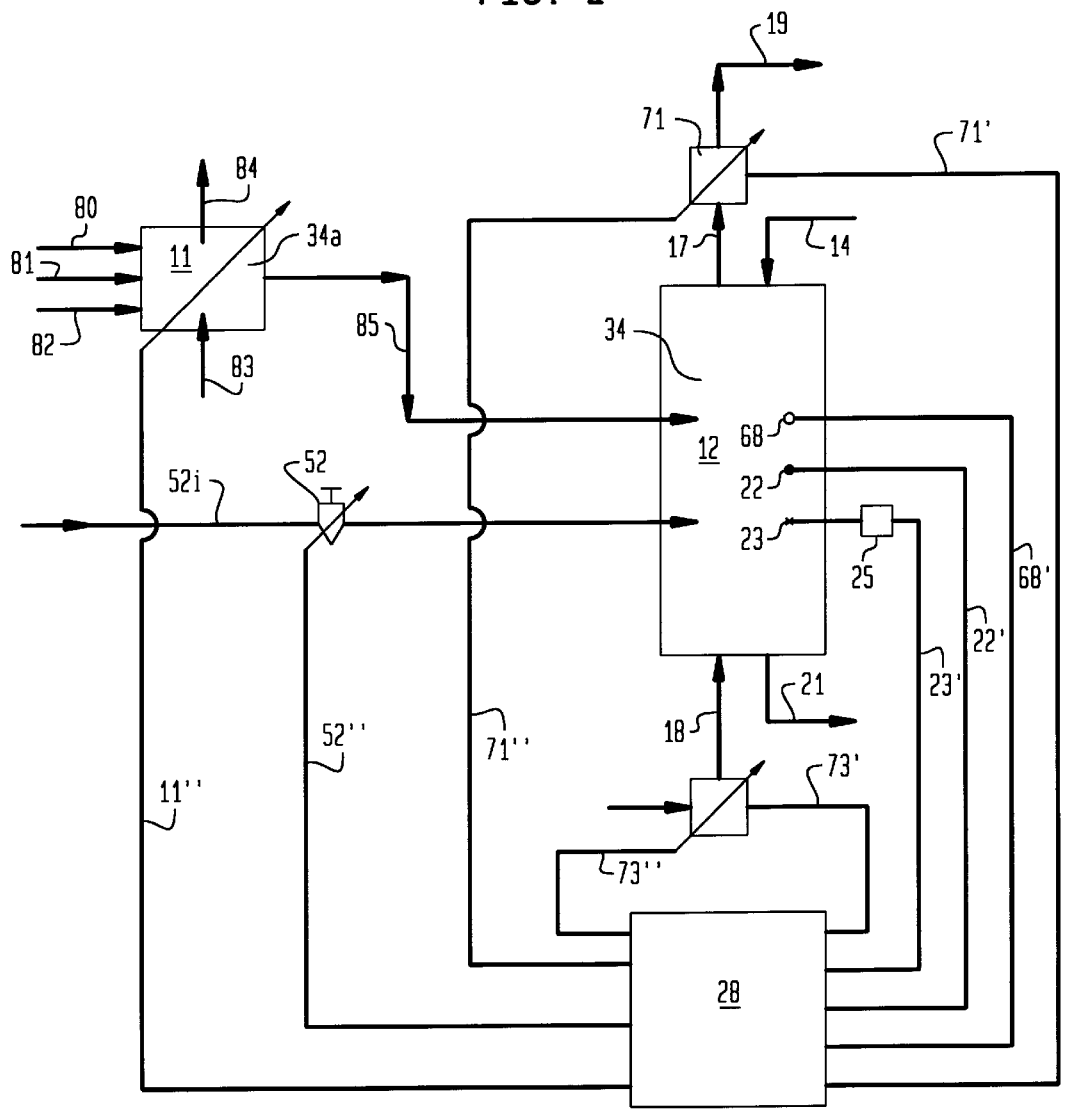
FIG. 2 illustrates schematically a different preferred embodiment of the present invention, wherein a precursory reaction chamber 11 is utilized, in addition to the major reaction chamber 12, for forming a mixture of hydrocarbon and rate-modulator having a desirable ratio.

In another preferred embodiment of the instant invention, better shown in FIG. 2, there is provided a precursory reaction chamber 11, which includes a precursory reaction zone 34a. A number of feeding inlet lines, line 80 for hydrocarbon, line 81 for initiator and line 82 for catalyst are connected to the precursory reaction chamber 11. Line 83 is for oxidant introduction, preferably oxygen or oxygen containing gas, and line 84 is for allowing off-gases to exit the precursory reaction chamber 11. The products of reaction are moved from the precursory reaction chamber 11 to the major reaction chamber 12 through line 85. The reaction parameters, such as flows, temperatures, pressure, etc., of the precursory reaction chamber 11 are controlled by the controller 28 through a multiple output line 11" by well known to the art techniques.

Auxiliary inlet lines (such as lines 50$i$, 54$i$, and 56$i$, for example, as shown in FIG. 1) may also be present for additional control of the final composition entering the major reaction chamber 12.

In operation of this embodiment, cyclohexane, initiator, such as for example cyclohexanone or acetaldehyde, and catalyst, such as for example cobalt salt, preferably in the absence of acidic solvent, are added to the precursory reaction chamber 11 through lines 80, 81, and 82, respectively. A gaseous oxidant, preferably comprising oxygen, enters the precursory reaction chamber through inlet line 83, and the off gases exit through outlet line 84. The product of oxidation, comprising cyclohexane and cyclohexanone, having a second ratio of cyclohexane to cyclohexanone, is fed to the major reaction chamber 12 for further oxidation to adipic acid. A solvent, such as acetic acid for example is also added to the major reaction chamber 12 through line 52$i$. The controller 28, as aforementioned, receives information related to oxidation rate in the major reaction chamber 12 through one or more of input lines 68', 22', 23', 71' and 73'. If the oxidation rate in the major reaction chamber 12 is higher than a desired range, the controller 28 changes the operational parameters of the precursory reaction chamber 11, in a manner to decrease the second ratio of cyclohexane to cyclohexanone in inlet line 85, until the oxidation rate in the major reaction chamber 12 falls within the desired range. Similarly, if the oxidation rate in the major reaction chamber 12 is lower than a desired range, the controller 28 changes the operational parameters of the precursory reaction chamber 11, in a manner to increase the second ratio of cyclohexane to cyclohexanone in inlet line 85, until the oxidation rate in the major reaction chamber 12 falls within the desired range. The desired range of the second ratio preferably falls between 99.5/0.5 and 95/10. However, this also depends on whether cyclohexane or cyclohexanone or a combination of cyclohexane and cyclohexanone are also fed directly to the major reaction chamber 12. Under such circumstances the above mentioned preferable limits of 99.5/0.5 and 95/10, are adjusted accordingly to take into account such additional feeding.

For example, increase of temperature, and/or increase of the initiator level, and/or the catalyst level entering the precursory reaction chamber 11, as ordered by the controller 28, decrease the second ratio of cyclohexane to cyclohexanone. A decrease in these operational parameters, among others, as ordered by the controller 28 through multiple output line 1", has an opposite result. Also an increase in hold-up time in the precursory chamber 11, results in a decreased cyclohexane to cyclohexanone second ratio. A decrease in hold-up time in the precursory chamber 11, results to an increased cyclohexane to cyclohexanone second ratio.

It is preferable that the oxidation in the precursory reaction chamber 11 takes place in the absence of solvent, while the oxidation in the major reaction chamber 12 takes place in the presence of a solvent, such as acetic acid for example.

Additional inlet lines (not shown) may introduce to the major reaction chamber more cyclohexane and/or cyclohexanone so that the second ratio is modified to become a desirable third ratio suitable to bring the oxidation rate within a desirable range.

Figure 3:
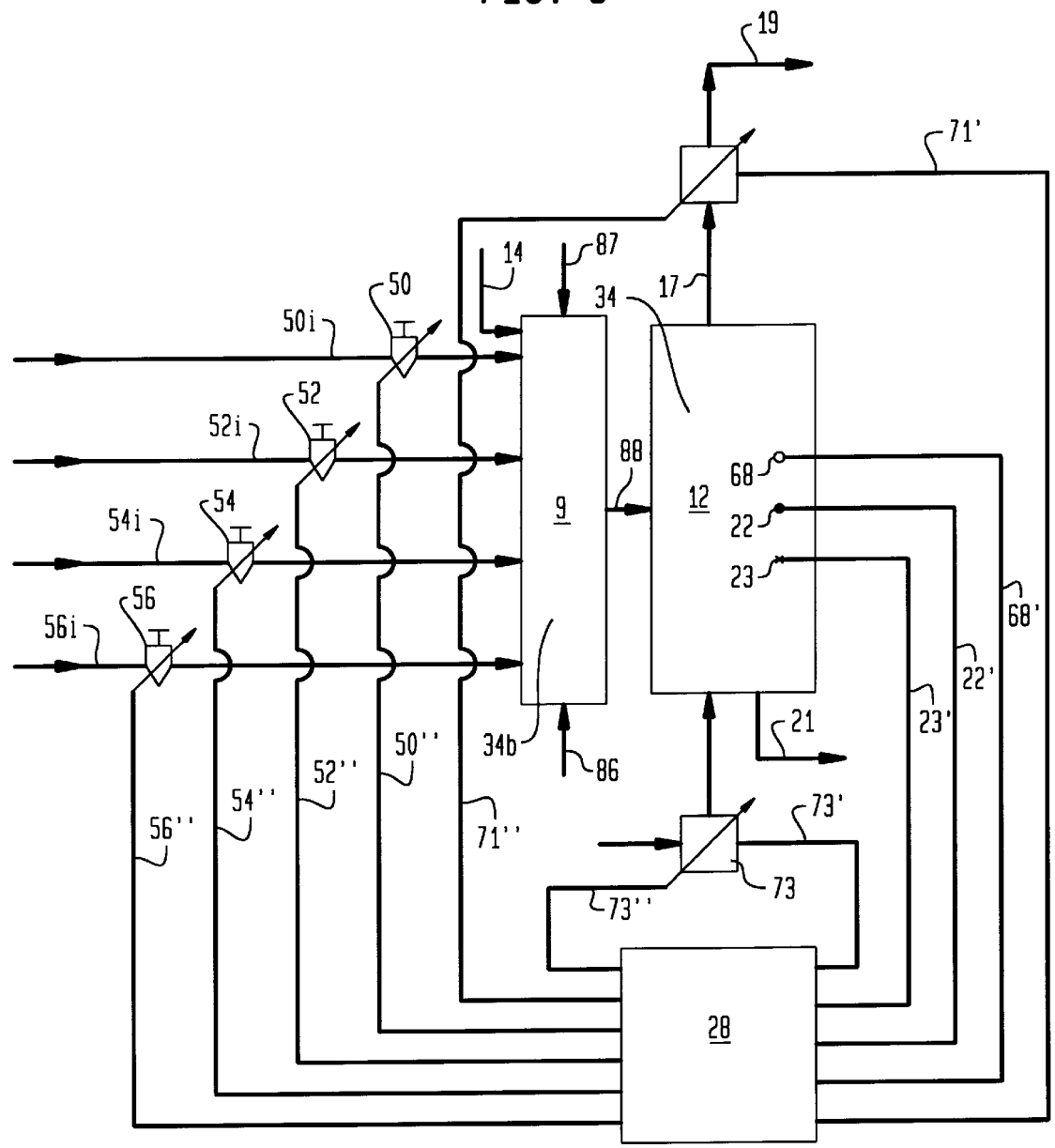
FIG. 3 illustrates schematically a still different preferred embodiment of the present invention, wherein a preceding reaction chamber 9 is utilized, in addition to the major reaction chamber 12, operated at a higher temperature than the major reaction chamber 12.

In still a different preferred embodiment of the instant invention, better shown in FIG. 3, there is provided a preceding reaction chamber 9, which includes a preceding reaction zone 34b. The preceding reaction chamber 9 is fed by lines 50i, 52i, 54i, 56i, and 14 (recyclables after reaction in major reaction chamber 12), either directly or after a pre-mixing chamber (not shown) and/or after a heat exchanger (not shown). A gaseous oxidant, preferably comprising oxygen, enters the preceding reaction chamber 9 through inlet line 86, and the off gases exit through outlet line 87. Line 88 connects the preceding reaction chamber 9 with the major reaction chamber 12 for moving matter from the preceding reaction chamber 9 to the major reaction chamber 12. The preceding reaction chamber 9 is connected (not shown for purposes of clarity) with the controller 28 through input and output lines, similar to the input and output lines connecting the controller 28 with the major reaction chamber 12.

In operation of this embodiment, the oxidation temperature in the preceding reaction chamber 9 and the preceding reaction zone 34b is set by the controller higher than the temperature in the major reaction chamber 12. Recyclables enter the preceding reaction chamber 9, as well as one or more of hydrocarbon, solvent, catalyst and rate modulator, through lines 50i, 52i, 54i, 56i, respectively, in amounts regulated by valves 50, 52, 54, and 56, respectively, which valves are in turn regulated by the controller 28 through output lines 50", 52", 54", and 56", respectively. The conversion of cyclohexane to adipic acid in the preceding reaction chamber 9, as measured in line 88, is preferably low, preferably in the range of 0.01% to 5%, more preferably in the range of 0.1% to 3%, and even more preferably in the order of 0.5% to 1%. The rest of the conversion, as measured in line 21, is preferably less than 80%, and more preferably less than 40%. However conversions in other ranges are not excluded.

The controller, based on information regarding oxygen consumption in the major reaction chamber 12, which is representative of oxidation rate, especially after correction for carbon monoxide and carbon dioxide formation, adjusts the ratio of hydrocarbon to rate modulator entering the preceding reaction chamber 9 so that the reaction or oxidation rate in the major reaction chamber 12 is maintained within desired limits. The adjustment is predominantly made by regulating valves 50 and 56 after taking into account the composition of the recyclables.

If the rate of oxidation is too high, the controller 28 changes the settings of valves 50 and 56 so that the ratio of hydrocarbon to rate-modulator is increased. Similarly, if the rate of oxidation is too low, the controller 28 changes the settings of valves 50 and 56 so that the ratio of hydrocarbon to rate-modulator is decreased.

In the case that the hydrocarbon is cyclohexane and the rate-modulator is cyclohexanone, an initial ratio of 97 to 3 is preferable. As the oxidation proceeds, the ratio may preferably be varied in the range of 99.9/0.1 to 80/20, and more preferably in the range of 99/1 to 90/10. Ratios lower than 80/20 usually produce large amounts of undesired by-products, while ratios higher than 99.9/0.1 are ineffective.

Changes and adjustments in the ratio of hydrocarbon to rate-modulator are preferably made in frequency of time increments ranging from 1/5 to 1/50 of the hold-up time of the contents of the major reaction chamber 12 in the case of stirred tank reactors. The controller 28 may control the timing, frequency and magnitude of such changes and adjustments, depending on the dynamics of the system, according to a desired program. If the feedback to the controller shows large effects with an adjustment, the frequency of a next adjustment is preferably decreased and/or the magnitude of the adjustment is also decreased. Similarly, if the feedback to the controller shows small effects with an adjustment, the frequency of a next adjustment is preferably increased and/or the magnitude of the adjustment is also increased.

A dual reaction chamber, as described above is useful in achieving higher output without sacrificing yield excessively.

Oxidations according to this invention, are non-destructive oxidations, wherein the oxidation product is different than carbon monoxide, carbon dioxide, and a mixture thereof. Of course, small amounts of these compounds may be formed along with the oxidation product, which may be one product or a mixture of products.

Examples include, but of course, are not limited to preparation of $C_5$–$C_{12}$ aliphatic dibasic acids from the corresponding saturated cycloaliphatic hydrocarbons, such as for example preparation of adipic acid from cyclohexane.

Regarding adipic acid, the preparation of which is especially suited to the methods and apparatuses of this invention, general information may be found in a plethora of U.S. Patents, among other references. These, include, but are not limited to:

U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); 4,263,453; 4,331,608; 4,606,863; 4,902,827; 5,221,800; and 5,321,157.

Diacids (for example adipic acid, phthalic acid, isophthalic acid, terephthalic acid, and the like) or other suitable compounds may be reacted, according to well known to the art techniques, with a third reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by well known to the art techniques to form fibers.

Examples demonstrating the operation of the instant invention have been given for illustration purposes only, and should not be construed as limiting the scope of this invention in any way. In addition it should be stressed that the preferred embodiments discussed in detail hereinabove, as well as any other embodiments encompassed within the limits of the instant invention, may be practiced individually, or in any combination thereof, according to common sense and/or expert opinion. Individual sections of the embodiments may also be practiced individually or in combination with other individual sections of embodiments or embodiments in their totality, according to the present invention. These combinations also lie within the realm of the present invention. Furthermore, any attempted explanations in the discussion are only speculative and are not intended to narrow the limits of this invention.

All explanations given hereinabove are to be considered as speculative and should not be construed as limiting the breadth of the claims.

What is claimed is:

1. A method of controlling the oxidation rate of a C5–C12 cycloaliphatic hydrocarbon to the corresponding dibasic acid, comprising the steps of:
   (a) feeding continually into a major reaction zone the cycloaliphatic hydrocarbon an oxidant, a rate-modulator, a catalyst, and a solvent comprising an organic acid containing only primary and/or secondary hydrogen atoms, the cycloaliphatic hydrocarbon and the rate-modulator being fed at a first hydrocarbon to rate-modulator ratio the first ratio being 80/20 or higher;
   (b) causing the oxidant to react with the cycloaliphatic hydrocarbon;
   (c) monitoring reaction rate and the first hydrocarbon to rate-modulator ratio; and
   (d) maintaining the reaction rate within, or directing the reaction rate toward a predetermined range, by making adjustments comprising steps of increasing the first hydrocarbon to rate-modulator ratio if the reaction rate is found in step (c) to be above the predetermined range, until the reaction rate falls within the predetermined range and decreasing the first hydrocarbon to rate-modulator ratio if the reaction rate is found in step (c) to be under the predetermined range, until the reaction rate falls within the predetermined range.

2. A method as defined in claim 1, wherein the first ratio is adjusted continually based on feedback relative to oxidation progress parameters.

3. A method as defined in claim 1, wherein the first ratio is kept substantially constant at steady state conditions of the oxidation.

4. A method as defined in claim 1, wherein the first ratio takes a path of predetermined values.

5. A method as defined in claim 1, wherein the rate-modulator comprises a hydrocarbon oxidation initiator.

6. A method as defined in claim 2, wherein the rate-modulator comprises a hydrocarbon oxidation initiator.

7. A method as defined in claim 3, wherein the rate-modulator comprises a hydrocarbon oxidation initiator.

8. A method as defined in claim 4, wherein the rate-modulator comprises a hydrocarbon oxidation initiator.

9. A method as defined in claim 1, wherein the rate-modulator is selected from a group consisting of an aldehyde corresponding to the organic acid of the solvent, a ketone corresponding to the cycloaliphatic hydrocarbon, a peroxide, and a mixture thereof.

10. A method as defined in claim 2, wherein the rate-modulator is selected from a group consisting of an aldehyde corresponding to the organic acid of the solvent, a ketone corresponding to the cycloaliphatic hydrocarbon, a peroxide, and a mixture thereof.

11. A method as defined in claim 3, wherein the rate-modulator is selected from a group consisting of an aldehyde corresponding to the organic acid of the solvent, a ketone corresponding to the cycloaliphatic hydrocarbon, a peroxide, and a mixture thereof.

12. A method as defined in claim 4, wherein the rate-modulator is selected from a group consisting of an aldehyde corresponding to the organic acid of the solvent, a ketone corresponding to the cycloaliphatic hydrocarbon, a peroxide, and a mixture thereof.

13. A method as defined in claim 9, wherein the rate-modulator is selected from a group consisting of an aldehyde corresponding to the organic acid of the solvent, a ketone corresponding to the cycloaliphatic hydrocarbon, and a mixture thereof.

14. A method as defined in claim 10, wherein the rate-modulator is selected from a group consisting of an aldehyde corresponding to the organic acid of the solvent, a ketone corresponding to the cycloaliphatic hydrocarbon, and a mixture thereof.

15. A method as defined in claim 11, wherein the rate-modulator is selected from a group consisting of an aldehyde corresponding to the organic acid of the solvent, a ketone corresponding to the cycloaliphatic hydrocarbon, and a mixture thereof.

16. A method as defined in claim 12, wherein the rate-modulator is selected from a group consisting of an aldehyde corresponding to the organic acid of the solvent, a ketone corresponding to the cycloaliphatic hydrocarbon, and a mixture thereof.

17. A method as defined in claim 13, wherein the rate-modulator comprises a ketone corresponding to the cycloaliphatic hydrocarbon.

18. A method as defined in claim 14, wherein the rate-modulator comprises a ketone corresponding to the cycloaliphatic hydrocarbon.

19. A method as defined in claim 15, wherein the rate-modulator comprises a ketone corresponding to the cycloaliphatic hydrocarbon.

20. A method as defined in claim 16, wherein the rate-modulator comprises a ketone corresponding to the cycloaliphatic hydrocarbon.

21. A method as defined in claim 17, wherein the rate-modulator comprises cyclohexanone, the aliphatic hydrocarbon comprises cyclohexane, the solvent comprises acetic acid, the oxidant comprises oxygen, and the catalyst comprises cobalt species.

22. A method as defined in claim 18, wherein the rate-modulator comprises cyclohexanone, the aliphatic hydrocarbon comprises cyclohexane, the solvent comprises acetic acid, the oxidant comprises oxygen, and the catalyst comprises cobalt species.

23. A method as defined in claim 19, wherein the rate-modulator comprises cyclohexanone, the aliphatic hydrocarbon comprises cyclohexane, the solvent comprises acetic acid, the oxidant comprises oxygen, and the catalyst comprises cobalt species.

24. A method as defined in claim 20, wherein the rate-modulator comprises cyclohexanone, the aliphatic hydrocarbon comprises cyclohexane, the solvent comprises acetic acid, the oxidant comprises oxygen, and the catalyst comprises cobalt species.

25. A method as defined in claim 21, wherein the oxidation rate is determined by a step of monitoring oxidant depletion in the major reaction zone and/or pressure variations in the major reaction zone and/or gas flow differentials between gases entering and gases exiting the major reaction zone.

26. A method as defined in claim 22, wherein the oxidation rate is determined by a step of monitoring oxygen depletion in the major reaction zone and/or pressure variations in the major reaction zone and/or gas flow differentials between gases entering and gases exiting the major reaction zone.

27. A method as defined in claim 1, further comprising a step of premixing the rate-modulator with at least one of solvent, catalyst, and hydrocarbon to form a first mixture, and then feeding said first mixture into the major reaction zone.

28. A method as defined in claim 27, further comprising a step of atomizing the first mixture in the major reaction zone.

29. A method as defined in claim 2, further comprising a step of premixing the rate-modulator with at least one of solvent, catalyst, and hydrocarbon to form a first mixture, and then feeding said first mixture into the major reaction zone.

30. A method as defined in claim 29, further comprising a step of atomizing the first mixture in the major reaction zone.

31. A method as defined in claim 3, further comprising a step of premixing the rate-modulator with at least one of solvent, catalyst, and hydrocarbon to form a first mixture, and then feeding said first mixture into the major reaction zone.

32. A method as defined in claim 31, further comprising a step of atomizing the first mixture in the major reaction zone.

33. A method as defined in claim 4, further comprising a step of premixing the rate-modulator with at least one of solvent, catalyst, and hydrocarbon to form a first mixture, and then feeding said first mixture into the major reaction zone.

34. A method as defined in claim 33, further comprising a step of atomizing the first mixture in the major reaction zone.

35. A method as defined in claim 5, further comprising a step of premixing the rate-modulator with at least one of solvent, catalyst, and hydrocarbon to form a first mixture, and then feeding said first mixture into the major reaction zone.

36. A method as defined in claim 35, further comprising a step of atomizing the first mixture in the major reaction zone.

37. A method as defined in claim 9, further comprising a step of premixing the rate-modulator with at least one of solvent, catalyst, and hydrocarbon to form a first mixture, and then feeding said first mixture into the major reaction zone.

38. A method as defined in claim 37, further comprising a step of atomizing the first mixture in the major reaction zone.

39. A method as defined in claim 13, further comprising a step of premixing the rate-modulator with at least one of solvent, catalyst, and hydrocarbon to form a first mixture, and then feeding said first mixture into the major reaction zone.

40. A method as defined in claim 39, further comprising a step of atomizing the first mixture in the major reaction zone.

41. A method as defined in claim 17, further comprising a step of premixing the rate-modulator with at least one of solvent, catalyst, and hydrocarbon to form a first mixture, and then feeding said first mixture into the major reaction zone.

42. A method as defined in claim 41, further comprising a step of atomizing the first mixture in the major reaction zone.

43. A method as defined in claim 21, further comprising a step of premixing the rate-modulator with at least one of solvent, catalyst, and hydrocarbon to form a first mixture, and then feeding said first mixture into the major reaction zone.

44. A method as defined in claim 43, further comprising a step of atomizing the first mixture in the major reaction zone.

45. A method of controlling the oxidation rate of cyclohexane to adipic acid, comprising the steps of:
   (a) partially oxidizing cyclohexane to a second mixture comprising cyclohexanone, the second mixture having a desired second ratio of cyclohexane to cyclohexanone, the second ratio being equal or higher than 80/20;
   (b) feeding the mixture into a major reaction zone in the presence of a catalyst, a solvent and an oxidant, and under conditions causing formation of adipic acid;
   (c) adjusting said desired second ratio in a manner that the oxidation rate falls within a desired range.

46. A method as defined in claim 45, further comprising a step of feeding additional cyclohexane or cyclohexanone to the major reaction zone for modifying said desired second ratio to become a desired third ratio.

47. A method as defined in claim 45, wherein the second ratio is adjusted continually based on feedback relative to oxidation progress parameters.

48. A method as defined in claim 45, wherein the second ratio is kept substantially constant at steady state conditions of the oxidation.

49. A method as defined in claim 45, wherein the second ratio takes a path of predetermined values.

50. A method as defined in claim 46, wherein the third ratio is adjusted continually based on feedback relative to oxidation progress parameters.

51. A method as defined in claim 46, wherein the third ratio is kept substantially constant at steady state conditions of the oxidation.

52. A method as defined in claim 46, wherein the third ratio takes a path of predetermined values.

53. A method as defined in claim 45, wherein the oxidation rate is determined by a step of monitoring oxidant depletion in the major reaction zone and/or pressure variations in the major reaction zone and/or gas flow differentials between gases entering and gases exiting the major reaction zone.

54. A method as defined in claim 46, wherein the oxidation rate is determined by a step of monitoring oxidant depletion in the major reaction zone and/or pressure variations in the major reaction zone and/or gas flow differentials between gases entering and gases exiting the major reaction zone.

55. A method as defined in claim 47, wherein the oxidation rate is determined by a step of monitoring oxidant depletion in the major reaction zone and/or pressure variations in the major reaction zone and/or gas flow differentials between gases entering and gases exiting the major reaction zone.

56. A method as defined in claim 48, wherein the oxidation rate is determined by a step of monitoring oxidant depletion in the major reaction zone and/or pressure variations in the major reaction zone and/or gas flow differentials between gases entering and gases exiting the major reaction zone.

57. A method as defined in claim 49, wherein the oxidation rate is determined by a step of monitoring oxidant depletion in the major reaction zone and/or pressure variations in the major reaction zone and/or gas flow differentials between gases entering and gases exiting the major reaction zone.

58. A method as defined in claim 50, wherein the oxidation rate is determined by a step of monitoring oxidant depletion in the major reaction zone and/or pressure variations in the major reaction zone and/or gas flow differentials between gases entering and gases exiting the major reaction zone.

59. A method as defined in claim 51, wherein the oxidation rate is determined by a step of monitoring oxidant depletion in the major reaction zone and/or pressure variations in the major reaction zone and/or gas flow differentials between gases entering and gases exiting the major reaction zone.

60. A method as defined in claim 52, wherein the oxidation rate is determined by a step of monitoring oxidant depletion in the major reaction zone and/or pressure variations in the major reaction zone and/or gas flow differentials between gases entering and gases exiting the major reaction zone.

61. A method as defined in claim 45, further comprising a step of atomizing the second mixture in the major reaction zone.

62. A method as defined in claim 46, further comprising a step of atomizing the second mixture in the major reaction zone.

63. A method as defined in claim 47, further comprising a step of atomizing the second mixture in the major reaction zone.

64. A method as defined in claim 48, further comprising a step of atomizing the second mixture in the major reaction zone.

65. A method as defined in claim 49, further comprising a step of atomizing the second mixture in the major reaction zone.

66. A method as defined in claim 50, further comprising a step of atomizing the second mixture in the major reaction zone.

67. A method as defined in claim 51, further comprising a step of atomizing the second mixture in the major reaction zone.

68. A method as defined in claim 52, further comprising a step of atomizing the second mixture in the major reaction zone.

69. A method as defined in claim 53, further comprising a step of atomizing the second mixture in the major reaction zone.

70. A method as defined in claim 54, further comprising a step of atomizing the second mixture in the major reaction zone.

71. A method as defined in claim 55, further comprising a step of atomizing the second mixture in the major reaction zone.

72. A method as defined in claim 56, further comprising a step of atomizing the second mixture in the major reaction zone.

73. A method as defined in claim 57, further comprising a step of atomizing the second mixture in the major reaction zone.

74. A method as defined in claim 58, further comprising a step of atomizing the second mixture in the major reaction zone.

75. A method as defined in claim 59, further comprising a step of atomizing the second mixture in the major reaction zone.

76. A method as defined in claim 60, further comprising a step of atomizing the second mixture in the major reaction zone.

77. A method as described in claim 1, wherein the oxidation takes place in a preceding reaction zone and the major reaction zone, the preceding reaction zone being at a higher temperature than the major reaction zone.

78. A method as described in claim 13, wherein the oxidation takes place in a preceding reaction zone and the major reaction zone, the preceding reaction zone being at a higher temperature than the major reaction zone.

79. A method as described in claim 17, wherein the oxidation takes place in a preceding reaction zone and the major reaction zone, the preceding reaction zone being at a higher temperature than the major reaction zone.

80. A method as described in claim 21, wherein the oxidation takes place in a preceding reaction zone and the major reaction zone, the preceding reaction zone being at a higher temperature than the major reaction zone.

81. A method as described in claim 25, wherein the oxidation takes place in a preceding reaction zone and the major reaction zone, the preceding reaction zone being at a higher temperature than the major reaction zone.

82. A method as described in claim 27, wherein the oxidation takes place in a preceding reaction zone and the major reaction zone, the preceding reaction zone being at a higher temperature than the major reaction zone.

83. A method as described in claim 28, wherein the oxidation takes place in a preceding reaction zone and the major reaction zone, the preceding reaction zone being at a higher temperature than the major reaction zone.

84. A method of making a polymer from a dibasic acid with a reactant selected from a group consisting of a polyol, a polyamine, and a polyamide in a manner to form a polymer of a polyester, or a polyamide, or a (polyimide and/or polyamideimide), respectively, the dibasic acid having been prepared from a respective hydrocarbon by steps of:

(a) feeding continually into a major reaction zone an oxidant and a rate-modulator in the presence of a catalyst and a solvent, under conditions causing oxidation of the hydrocarbon to the dibasic acid by the oxidant, the hydrocarbon and the rate-modulator being fed at a first ratio, the solvent comprising an organic acid containing only primary and/or secondary hydrogen atoms; and (b) adjusting said first ratio in a manner that the oxidation rate falls within a range of desired values.

85. A method as defined in claim 84, further comprising a step of spinning the polymer into fibers.

86. A method as defined in claim 84, wherein the rate-modulator is selected from a group consisting of an aldehyde corresponding to the organic acid of the solvent, a ketone corresponding to the cycloaliphatic hydrocarbon, a peroxide, and a mixture thereof.

87. A method as defined in claim 86, further comprising a step of spinning the polymer into fibers.

88. A method as defined in claim 84, wherein the oxidation rate is determined by a step of monitoring oxidant depletion in the major reaction zone and/or pressure variations in the major reaction zone and/or gas flow differentials between gases entering and gases exiting the major reaction zone.

89. A method as defined in claim 88, further comprising a step of spinning the polymer into fibers.

90. A method of making a polymer from a dibasic acid with a reactant selected from a group consisting of a polyol, a polyamine, and a polyamide in a manner to form a polymer of a polyester, or a polyamide, or a (polyimide and/or polyamideimide), respectively, the dibasic acid having been prepared from a respective hydrocarbon by steps of:

(a) partially oxidizing cyclohexane to a second mixture comprising cyclohexanone, the second mixture having a desired second ratio of cyclohexane to cyclohexanone;

(b) feeding the mixture into a major reaction zone in the presence of a catalyst, a solvent and an oxidant, and under conditions causing formation of adipic acid;

(c) adjusting said desired second ratio in a manner that the oxidation rate falls within a desired range.

91. A method as defined in claim 90, further comprising a step of spinning the polymer into fibers.

* * * * *

UNITED STATES PATENT AND TRADEMARK OFFICE
CERTIFICATE OF CORRECTION

PATENT NO. : 6,103,933
DATED : August 15, 2000
INVENTOR(S) : David C. DeCoster et al.

Page 1 of 1

It is certified that error appears in the above-identified patent and that said Letters Patent is hereby corrected as shown below:

Claim 1, Column 17:
Line 6, should read --hydrocarbon, an oxidant, --.

Claim 1, Column 17:
Line 11, should read --rate-modulator ratio, the first ratio--.

Claim 1, Column 17:
Line 23, should read --range, and decreasing--.

Signed and Sealed this

Twelfth Day of June, 2001

*Attest:*

Nicholas P. Godici

*Attesting Officer*

NICHOLAS P. GODICI
*Acting Director of the United States Patent and Trademark Office*